(12) United States Patent  
Tirtowidjojo et al.

(10) Patent No.: US 8,926,918 B2  
(45) Date of Patent: Jan. 6, 2015

(54) ISOTHERMAL MULTITUBE REACTORS

(71) Applicant: Dow Global Technologies LLC, Midland, MI (US)

(72) Inventors: Max Markus Tirtowidjojo, Lake Jackson, TX (US); Hua Bai, Lake Jackson, TX (US); Debashis Chakraborty, Lake Jackson, TX (US); Juergen Eiffler, Stade (DE); Heinz Groenewald, Hammah (DE); Kurt Frederick Hirsekorn, Midland, MI (US); Manfred Kokott, Stade (DE); William J. Kruper, Jr., Sanford, MI (US); Thomas Ulrich Luebbe, Stade (DE); Avani Maulik Patel, Midland, MI (US); Shirley Shaw Sexton, Cypress, TX (US); Peter Wenzel, Buxtehude (DE); Marcus Wobser, Stade (DE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/024,023

(22) Filed: Sep. 11, 2013

(65) Prior Publication Data

US 2014/0010741 A1 Jan. 9, 2014

Related U.S. Application Data

(62) Division of application No. 12/901,305, filed on Oct. 8, 2010, now Pat. No. 8,558,041.

(60) Provisional application No. 61/250,030, filed on Oct. 9, 2009.

(51) Int. Cl.
*B01J 19/24* (2006.01)
*B01J 8/06* (2006.01)

(Continued)

(52) U.S. Cl.
CPC .......... *B01J 19/2425* (2013.01); *B01J 19/0026* (2013.01); *B01J 19/006* (2013.01);

(Continued)

(58) Field of Classification Search
CPC ............. F27B 15/14; F28D 7/00; F28D 7/16; B01J 8/06; B01J 19/2415

USPC .......................... 422/139, 146, 198, 200, 201
See application file for complete search history.

(56) References Cited

U.S. PATENT DOCUMENTS

| 2,119,484 A | 5/1938 | Levine |
| 2,179,378 A | 11/1939 | Metzger |

(Continued)

FOREIGN PATENT DOCUMENTS

| CH | 609022 | 6/1974 |
| CN | 101492341 | 7/2009 |
| CN | 101544535 | 9/2009 |
| CN | 101913979 | 12/2010 |
| CN | 101913980 | 12/2010 |

(Continued)

OTHER PUBLICATIONS

Bai et al., "Isomerization of Tetrachloropropene to Promote Utilization Ratio of Triallate Raw Materials", Petrochemical Technology & Application, 2007, 25(1).

(Continued)

*Primary Examiner* — Walter D Griffin
*Assistant Examiner* — Huy-Tram Nguyen
(74) *Attorney, Agent, or Firm* — Lois K. Ruszala; KSJLAW, LLC

(57) ABSTRACT

The present invention provides isothermal multitube reactors suitable for the production of chlorinated and/or fluorinated propene and higher alkenes from the reaction of chlorinated and/or fluorinated alkanes and chlorinated and/or fluorinated alkenes. The reactors utilize a feed mixture inlet temperature at least 20° C. different from a desired reaction temperature.

10 Claims, 3 Drawing Sheets

(51) Int. Cl.
*F28D 7/00* (2006.01)
*F28D 7/16* (2006.01)
*F27B 15/14* (2006.01)
*B01J 19/00* (2006.01)
*C07C 17/20* (2006.01)
*C07C 17/269* (2006.01)

(52) U.S. Cl.
CPC .......... *B01J 19/2405* (2013.01); *C07C 17/206* (2013.01); *C07C 17/269* (2013.01); *B01J 2219/00063* (2013.01); *B01J 2219/00081* (2013.01); *B01J 2219/00159* (2013.01); *B01J 2219/00162* (2013.01); *B01J 2219/00166* (2013.01); *B01J 2219/00247* (2013.01); *B01J 2219/0227* (2013.01)
USPC ........... 422/201; 422/139; 422/146; 422/198; 422/200

(56) References Cited

U.S. PATENT DOCUMENTS

| | | |
|---|---|---|
| 2,207,193 A | 7/1940 | Groll |
| 2,299,441 A | 10/1942 | Vaughan |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A * | 9/1956 | Monroe et al. ................. 277/606 |
| 2,765,359 A | 10/1956 | Pichler |
| 2,964,579 A * | 12/1960 | Weller et al. ................... 585/260 |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A * | 5/1969 | Fernald et al. ................. 585/503 |
| 3,446,859 A | 5/1969 | Weil |
| 3,502,734 A | 3/1970 | Baird |
| 3,525,595 A | 8/1970 | Zirngibl et al. |
| 3,551,512 A * | 12/1970 | Loeffler, Jr. et al. .......... 585/541 |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,926,758 A | 12/1975 | Smith |
| 3,948,858 A | 4/1976 | Weirsum |
| 3,954,410 A | 5/1976 | Pohl |
| 4,038,372 A | 7/1977 | Colli |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A * | 2/1987 | Hunter ..................... 122/235.14 |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A * | 3/1991 | Cox et al. ....................... 210/137 |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,254,771 A | 10/1993 | Cremer |
| 5,254,772 A | 10/1993 | Dukat |
| 5,254,788 A * | 10/1993 | Gartside et al. ................ 585/659 |
| 5,262,575 A | 11/1993 | Dianis |
| 5,315,044 A | 5/1994 | Furutaka |
| 5,414,166 A | 5/1995 | Kim |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,472,573 B1 | 10/2002 | Yamamoto |
| 6,538,167 B1 * | 3/2003 | Brown et al. ................... 585/640 |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 * | 1/2004 | Zoeller et al. ................. 564/448 |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,880,040 B2 | 2/2011 | Mukhopadhyay |
| 7,951,982 B2 | 5/2011 | Mukhopadhyay |
| 8,058,486 B2 | 11/2011 | Merkel |
| 8,058,490 B2 | 11/2011 | Strebelle |
| 8,071,825 B2 | 12/2011 | Johnson |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Kruper |
| 8,258,355 B2 | 9/2012 | Merkel |
| 8,357,828 B2 | 1/2013 | Okamoto |
| 8,367,867 B2 | 2/2013 | Zardi |
| 8,581,012 B2 | 11/2013 | Tirtowidjojo |
| 8,614,363 B2 | 12/2013 | Wilson |
| 2001/0018962 A1 * | 9/2001 | Joshi et al. .................... 165/11.1 |
| 2002/0110711 A1 | 8/2002 | Boneberg |
| 2005/0131254 A1 * | 6/2005 | Yada et al. ..................... 562/545 |
| 2006/0150445 A1 | 7/2006 | Redding |
| 2006/0292046 A1 | 12/2006 | Fruchey |
| 2007/0112229 A1 | 5/2007 | Mukhopadhyay |
| 2007/0197841 A1 | 8/2007 | Mukhopadhyay |
| 2007/0265368 A1 | 11/2007 | Rao |
| 2007/0267176 A1 * | 11/2007 | Song et al. ....................... 165/84 |
| 2008/0021229 A1 | 1/2008 | Maughon |
| 2008/0073063 A1 * | 3/2008 | Clavenna et al. ................ 165/84 |
| 2008/0118018 A1 | 5/2008 | Schrauwen |
| 2008/0207962 A1 | 8/2008 | Rao |
| 2009/0018377 A1 | 1/2009 | Boyce |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |

(56) References Cited

U.S. PATENT DOCUMENTS

| | | | |
|---|---|---|---|
| 2009/0306438 | A1 | 12/2009 | Sievert |
| 2010/0041864 | A1 | 2/2010 | Kadowaki et al. |
| 2010/0185029 | A1 | 7/2010 | Elsheikh |
| 2010/0210883 | A1 | 8/2010 | Mukhopadhyay |
| 2010/0263278 | A1 | 10/2010 | Kowoll et al. |
| 2011/0083955 | A1 | 4/2011 | Tirtowidjojo |
| 2011/0172472 | A1 | 7/2011 | Sakyu |
| 2011/0218369 | A1 | 9/2011 | Elsheikh |
| 2011/0251425 | A1 | 10/2011 | Penzel |
| 2012/0035402 | A1 | 2/2012 | Wilson |
| 2012/0041239 | A1 | 2/2012 | Suzuki |
| 2012/0065434 | A1 | 3/2012 | Nose |
| 2014/0081055 | A1 | 3/2014 | Tirtowidjojo |

FOREIGN PATENT DOCUMENTS

| | | |
|---|---|---|
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| JP | S54-79207 | 6/1979 |
| JP | S54-135712 | 10/1979 |
| JP | 2001-151708 | 6/2001 |
| JP | 2001-213820 | 8/2001 |
| JP | 2006272267 A | 10/2006 |
| JP | 2007-021396 | 2/2007 |
| JP | 2008-063314 | 3/2008 |
| JP | 2009000592 A | 1/2009 |
| JP | 2009-046653 | 3/2009 |
| JP | 2011-144148 | 7/2011 |
| LU | 52247 | 12/1966 |
| SU | 899523 | 1/1982 |
| WO | 01/38275 | 5/2001 |
| WO | 01/38371 | 5/2001 |
| WO | 0138271 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |

OTHER PUBLICATIONS

Boualy et al., "Kharasch Addition of Tetrachloromethane to Alkenes Catalyzed by Metal Acetylacetonates", Catalysis Communications, 2011, pp. 1295-1297, vol. 12.

Chai et al., "Study of Preparation of 1,1,1,3-tetrachloropropane", Zhejiang Chemical Industry, 2010, pp. 1-3, 41(5).

Cristiano et al., "Tetraalkylphosphoniunn Trihalides. Room Temperature Ionic Liquids As Halogenation Reagents", J. Org. Chem., 2009, pp. 9027-9033, vol. 74.

Evstigneev et al., "Initiated Chlorination of Tetrachloropropane", Khim. Prom., 1984, pp. 393-394, 16(7).

Gault et al., "Chlorination of Chloroform", Comptes Rendus Des Seances De L'Academie des Sciences, 1924, pp. 467-469, vol. 179.

Gerding et al., "Raman Spectra of aliphatic chlorine compounds II. Chloroethenes and Chloropropenes", Recueil, Jan. 1, 1955, pp. 957-975, vol. 74.

Hatch et al., "Allylic Chlorides. XV. Preparation and Properties of the 1,2,3-Trichloropropenes", JACS, Jan. 5, 1952, pp. 123-126, 74(1).

Hatch et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte der Deutschen Chemischen Gesellschaft, May-Aug. 1893, pp. 1257-1261, 26(2).

Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).

Kang et al., "Kinetics of Synthesis of 1,1,1,3,3-pentachlorobutane Catalyzed by Fe-FeCl3", Chemical Research and Application, Jun. 2011, pp. 657-660, 23(6).

Kharasch et al., "Chlorinations with Sulfuryl Chloride. I. The Peroxide-Catalyzed Chlorination of Hydrocarbons", JACS, 1939, pp. 2142-2150, vol. 61.

Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper et al., "Synthesis of alpha-Halocinnamate Esters via Solvolytic Rearrangement of Trichloroallyl Alcohols", J. Org. Chem., 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al., "Thermocatalytic Reactions of Bromochloropropanes", Russian Journal of Physical Chemistry, Jan. 1, 1983, pp. 1142-1146, vol. 57.

Liu et al., "Progress in the Synthesis of 1,1,1,3-tetrachloropropane", Guangzhou Chemicals, 2011, pp. 41-42, 39(5).

McBee et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.

Nikishin et al., "Reactions of Methanol and Ethanol", Seriya Khimicheskaya, Dec. 1966, pp. 2188-2192, vol. 12.

Pozdnev et al., "Chlorination of Chloroform and the Conversion of Methylene Chloride Manufacture Still Residues", Khim., Khim. Tekhnol., 1970, 70(4).

Rotshtein et al., "Isomer Distribution on Chlorination of Chloropropanes", Zhurnal Organicheskoi Khimii, Sep. 1966, pp. 1539-1542, 2(9).

Semenov et al., "Selectivity of Photochemical Chlorination of Chloromethane in the Liquid Phase", Zhurnal Prikladnoi Khimii, Apr. 1985, pp. 840-845, 58(4).

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

(56) References Cited

OTHER PUBLICATIONS

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al., "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

Galitzenstein et al., "The Dehydrochlorination of Propylene Dichloride", Journal of the Society of Chemical Industry, 1950, pp. 298-304, vol. 69.

Fields et al., "Thermal Isomerization of 1,1-dichlorocyclopropanes", Chemical Communications (London) No. 21, Jan. 1, 1967, p. 1081.

Nguyen et al., "Condensation de chloroforme avec des olefins fluorees en milieu basique,"Journal of Fluorine Chemistry, vol. 55, No. 3, Dec. 1991, pp. 241-248.

Shelton et al., "Addition of Halogens and Halogen Compounds to Allylic Chlorides I. Addition of Hydrogen Halides," Journal of Organic Chemistry, 23, pp. 1876-1880 (1958).

Tobey et al., "Pentachlorocyclopropane 1" Journal of the American Chemical Society, vol. 88, No. 11, Jun. 1996 pp. 2478-2481.

Ochi, et al., "Preparation of Chloropropenes by Photochemical Dehydrochlorination of 1,2-Dichloropropane", Chemical Abstracts, Jul. 17, 1989, p. 574, 111(3).

\* cited by examiner

ISOTHERMAL MULTITUBE REACTORS

CROSS REFERENCE TO RELATED APPLICATIONS

This is a divisional application of U. S. patent application Ser. No. 12/901,305, filed Oct. 8, 2010, now U.S. Pat. No. 8,558,041, which claims benefit of U.S. provisional patent application Ser. No. 61/250,030, filed Oct. 9, 2009.

FIELD

The present invention relates to multitube reactors capable of near-isothermal operation and suitable for conducting continuous, gas phase, free radical reactions to produce chlorinated and/or fluorinated propene and higher alkenes. Processes incorporating the same are also provided.

BACKGROUND

Multitube reactors are ubiquitous in the manufacture of commodity chemicals. These reactors, which may comprise a normally substantially vertical vessel further comprising a plurality of open ended reactor tubes, are typically used for catalyzed gas-phase reactions. The shell of a multitube reactor for such processes may typically have a diameter of several meters and include from as few as about 5000 up to as many as about 50000 reaction tubes. Each reactor tube may be as long as 5, 10 or even 15 meters.

In such reactors, the upper ends of the reactor tubes may generally be affixed to an upper tube sheet and be in fluid communication with a fluid inlet head above the upper tube sheet. Similarly, the lower ends of the reactor tubes may generally be affixed to a lower tube sheet and in fluid communication with an effluent collecting head below the lower tube sheet. During normal operation, the desired reactant gases are supplied to the fluid inlet chamber at the upper ends of the reactor tubes and passed therethrough. Effluents leaving the lower ends of the reactor tubes are collected in the effluent collecting head. The heat of reaction is removed by a heat transfer fluid which is passed across the outer surfaces of the reactor tubes.

Due at least in part to the multiplicity of reactor tubes utilized, temperature control in multitube reactors can be challenging. Yet, precise temperature control may often be desirable, or even required, within many manufacturing processes. For example, accurate temperature control can be critical in maintaining the desired reaction rate. Process inhomogeneities, e.g., hot spots, if allowed to occur, can result in increased reaction rate and conversion, which for many reactions; can result in an undesirable decrease in selectivity. And, undesirable temperature fluctuations can detrimentally impact any thermally sensitive components or inputs utilized in the reaction. For example, undesirably fluctuating temperatures can lead to reduced catalyst life, and degradation of thermally sensitive components, which, in turn, can result in fouling of the reactor tubes.

When considering the challenge of appropriate temperature control within a multitube reactor and a process comprising the same, the residence time of reaction components within the process, and more particularly, at a particular temperature within the process, must also be considered. That is, the detrimental impact of ineffective temperature control may be exacerbated if reaction components have a residence time at the suboptimal temperature that allows for an increase in conversion and/or reaction or decomposition of thermally sensitive components.

It would thus be desirable to provide an improved multitube reactor, wherein such considerations have been taken into account, and the aforementioned challenges have been substantially overcome.

BRIEF DESCRIPTION

Such a reactor is provided herein. More specifically, the reactor described herein can provide not only more accurate temperature control via more effective heat transfer into and/or out of the reactor, but also, can provide appropriate residence times of reaction components so that desired conversions and/or selectivities can be seen. The reactor is thus particularly well suited for reactions comprising thermally sensitive components such as catalysts that may otherwise exhibit reduced lifetimes, or reaction components that undesirably react or decompose at temperatures within the processing specifications of the process desirably carried out within the reactor.

In one aspect of the present invention, an isothermal multitube reactor is provided comprising a plurality of reactor tubes situated within a shell. The reactor is suitable for use in a continuous, gas-phase, free radical process for the production of chlorinated and/or fluorinated propene and higher alkenes and utilizes a feed mixture temperature at least 20° C. lower than the desired reaction temperature. In some embodiments, the reactor may further comprise a design that minimizes the production of by-products at a desired conversion.

Several such designs are provided, including i) a design that facilitates heat transfer to and/or from the reactor; ii) a design that facilitates reduced backmixing or recirculation upon exit from, the reactor, and/or reduced formation of by-products during any backmixing that may occur; iii) a design that optimizes the flow of the reaction components at the boundary between the reaction components and at least a portion of at least one reactor tube wall; and/or iv) a design that facilitates a reduction of the temperature of a reactor effluent to a temperature below which substantial formation of by-products does not occur. Combinations of one or more of these may be utilized, in which case the benefits provided by one may be further leveraged, perhaps even synergistically, by addition of the other(s).

Since the present reactors are expected to provide time and cost savings to the continuous processes in which they are utilized, not only are processes utilizing the reactors provided, but the products produced thereby may be used to carry these advantages forward, i.e., to downstream processes, or to end-uses. And so, also provided herein are processes for the use of a chlorinated and/or fluorinated propene and higher alkene, which in some embodiments may be a chlorinated propene, produced in the present reactors to prepare a downstream product, which in some embodiments, may be 2,3,3,3-tetrafluoroprop-1-ene (HFO-1234yf) or 1,3,3,3-tetrafluoroprop-1-ene (HFO-1234ze).

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

Figure 1:
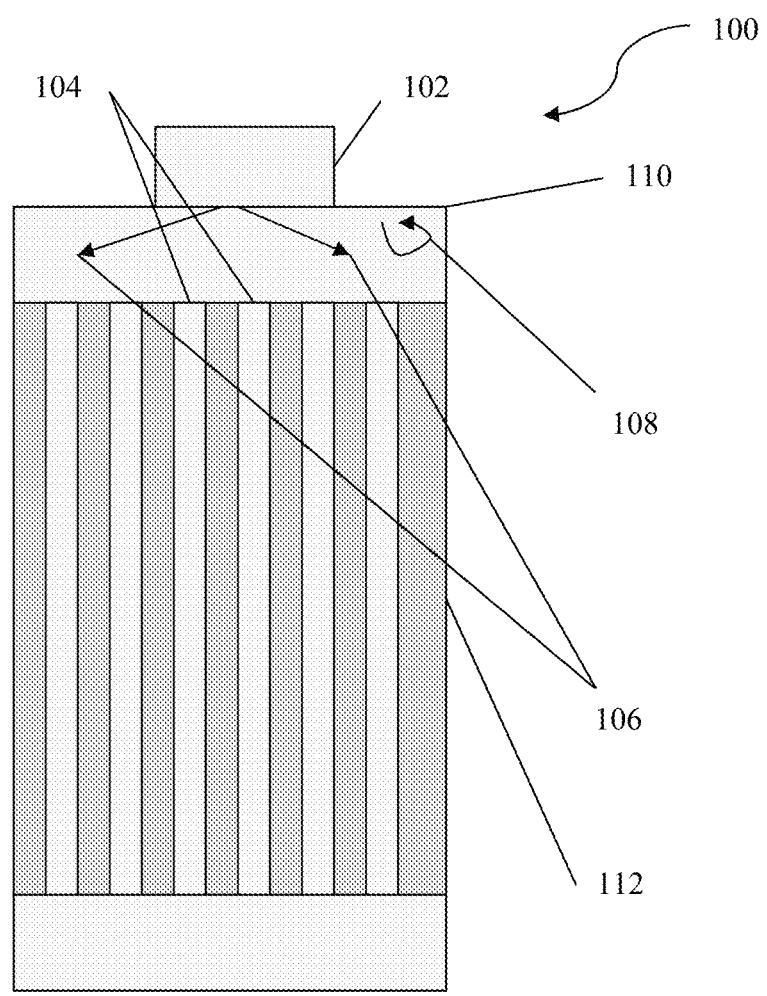
FIG. 1 is a schematic representation in cross-section of a conventional configuration of a multitube reactor and inlet therefore.

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not intended to limit the part being described limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The present invention provides an isothermal multitube reactor suitable for use in a continuous, gas-phase, free radical process for the production of chlorinated and/or fluorinated propene and higher alkenes. Although reference is made particularly to multitube reactors, it is to be understood that the reaction spaces provided within the reactor can be of any geometry, as can the shell surrounding them. That is, the reaction spaces can be defined by plates, so that they are generally in the form of slits, or, the reaction spaces may be defined by square, triangular, or oval tubes.

Advantageously, the reactor comprises a design that minimizes the production of by-products, including decomposition products of reaction components that may foul the reactor. In so doing, the percent conversion of the reaction carried out within the reactor may be kept within a desired range, e.g., the percent conversion of the reaction desirably increases by less than about 5%, or less than about 2%, or preferably, increases by less than about 1%, so that a high percent selectivity, e.g., 70% or greater, may be seen. Stated another way, at a limiting reagent conversion of at least about 5%, or at least about 10%, or at least about 15%, or even at least about 20%, selectivity to the desired product can be as high as about 70%, or about 75%, or about 80%, or even about 85% or greater. As such, the present reactor is particularly well suited for conducting reactions for which an increase in percent conversion may typically indicate increased production of reaction by-products, and thus, reduced percent selectivity.

The reactors described herein may be utilized in any continuous gas-phase, free radical process, and in particular, are well suited for such reactions that are also homogeneous and exothermic. The reactors described herein are also particularly appropriately employed for reactions involving at least one limiting reactant having a desired conversion far from exhaustion of the same, e.g., mass or molar conversions of less than 80%, or less than 40%, or even less than 20% of the limiting reactant. As discussed above, the present reactors are also particularly well suited for such reactions particularly susceptible to the formation of by-products, and the effects thereof on reaction selectivity, or comprising thermally sensitive components, e.g., that may react, or degrade, to form undesirable by-products. Thermally sensitive components may include, for example, reactants, products, catalysts, and even by-products which may further react or thermally degrade to form other by-products. Reactions comprising combinations of thermally sensitive components may also find benefit from being carried out in the present reactors. Even at such low conversions of limiting reagent, and when used to conduct reactions susceptible to the formation of by-products, the present reactors can provide selectivity to the desired product of at least about 70%, or about 75%, or about 80%, or even about 85% or greater.

One example of such reactions includes, but is not limited to, reactions that produce chlorinated and/or fluorinated propene and higher alkenes. Preferred alkenes include those having from about three to about six carbon atoms. Exemplary reactions include reactions of methanes, including chloromethanes, fluoromethanes, or chlorofluoromethanes, i.e., having the formula $CH_{4-a-b}Cl_aF_b$, wherein each a and b are independently 0-3 and 4-a-b is greater than 0; and chloroethlyenes or chlorofluoroethylenes to provide chlorinated and/or fluorinated propenes according to the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g<2, d+h<1, and e+f<3. Particular exemplary reactions include the reaction of methyl chloride with perchloroethylene to provide 1,1,2,3-tetrachloropropene, the reaction of methyl fluoride with perchloroethylene to provide 1,1,2-chloro-3-fluoro-propene and the reaction of methyl fluoride with trifluorochloroethylene to provide 1,1,2,3-tetrafluoropropene. However, these references are intended only to be exemplary and are not to be construed as limiting to the reactors and concepts described herein.

Many parameters are known in the chemical engineering art to be useful in adjusting the reaction conditions within multitube reactors, however, prior to the invention described herein, had either not been applied in a manner that resulted in a reduction in formation of by-products so that a desired conversion of the reactant to desired product can be seen, and/or to reactions particularly in need thereof. That is, it has now been discovered how to design a multitube reactor to be amenable for use in conducting continuous gas phase, free radical reactions comprising thermally sensitive reaction components, such as catalysts or initiators comprising chlorine, so that the reactions conducted therein have the desired percent conversions and product selectivity. Because of the unique chemistry involved in conducting continuous gas phase, free radical reactions comprising thermally sensitive reaction components, those of ordinary skill in the art would not necessarily consider isothermal multitube reactors as good candidates as reactors within which to conduct them.

For example, processes for the production of chlorinated or fluorinated propenes may typically result in the formation of larger quantities of reaction by-products than conventional halogenation processes. That is, In conventional free radical halogenation reactions, reactor promoted backmixing or recirculation such as that provided by jet stirred reactors, is typically considered to increase productivity of the reactor with little impact on byproduct formation [Liu et al, *Chemical Engineering Science* 59 (2004) 5167-5176]. In addition, jet stirred reactors are typically operated at adiabatic conditions, where heat transfer to the surroundings is minimized.

The formation of large quantities of by-products, in turn, can not only detrimentally impact process capacity and conversion, but can be problematic for other reasons as well, not the least of which being that the same can cause reactor fouling. Furthermore, the backmixing that necessarily occurs prior to entry into the reaction tubes in multitube reactors would encourage the formation of by-products in such reactions. And so, the present improved processes for the production of chlorinated and/or fluorinated propenes or higher alkenes thus allow for such backmixing to occur, while minimizing the formation of by-products. That is, a certain amount of backmixing and/or recirculation unavoidably occurs in the chamber head feed distributor prior to the entry of the feed into the reaction tubes in order for the reactions therein to occur within a commercially reasonable time and space.

It has also now been discovered that isothermal multitube reactors can be used for such processes if the inlet temperature is caused to be lower than the desired reaction temperature, or the temperature at which substantial amounts of by-products will form, by at least about 20° C., or by about 50° C., or by about 100° C. As such, the temperature at the inlet/mixer of the reactor is not conducive to the formation of by-products, and yet, the mixing of the reactants that needs to occur in the inlet/mixer can occur so that the reaction tubes and reactor size can be of an economical size. In terms of the exemplary reaction of methyl chloride with perchloroethylene to form 1,1,2,3-tetrachloropropene, an inlet temperature of less than about 370° C., or less than 325° C., would be suitable to discourage or prevent formation of by-products, such as tetrachlorobutenes, graphite, and other carbonaceous deposits.

This concept is further illustrated by FIG. 1, wherein a typical configuration of a multitube reactor 100 comprising inlet 102 is shown. As shown, due at least in part to the disparate geometrical configurations of reactor 100 and inlet/mixer 102, the flow of the reactants may generally proceed toward the inlets of reactor tubes 104 as shown by arrows 106. This flow pattern may create areas of backmixing and/or recirculation indicated by arrows 108. Without reconfiguring reactor 100 and/or inlet 102, the impact of any such backmixing or recirculation zone may be minimized by maintaining the temperature within region 110 at a lower temperature of 20° C., or preferably 50° C., or even more preferably 100° C. than the temperature required for the reaction components present to react to form significant amounts of by-products. As mentioned above, for the exemplary case of the reaction of methyl chloride and perchloroethylene to produce 1,1,2,3 perchloroethylene, a temperature of less than about 370° C., or less than about 325° C., would be sufficient for this purpose.

In some embodiments, the reactor may additionally comprise one or more other design features to further minimize the formation of by-products, or to reduce or eliminate the impact of any by-products that are formed. More particularly, the reactors provided herein may comprise one or more i) a design that facilitates heat transfer to and/or from the reactor; ii) a design that facilitates reduced backmixing or recirculation upon exit from, the reactor, and/or reduced formation of by-products during any backmixing or recirculation that may occur; iii) a design that optimizes the flow of the reaction components at the boundary between the reaction components and at least a portion of at least one reactor tube wall; and/or iv) a design that facilitates a reduction of the temperature of a reactor effluent to a temperature below which substantial formation of by-products does not occur. Any number of the reactor designs described herein may be used in any combination.

In some embodiments, the reactor provided herein may comprise a design that facilitates heat transfer to, from and/or within the reactor so that the reactor may operate substantially isothermally within the reaction zone. The term "isothermally" as applied to the multitube reactors described herein means that, at steady state conditions, the temperature within the reaction zone remains substantially constant, i.e., will vary only by about 10° C., or only by about 5° C. or even by only about 1° C., or even less, once the desired reaction temperature has been reached.

Various methodologies can be utilized to facilitate the heat transfer to and/or from the reactor, typically between the reactor tubes and the shell. Heat transfer fluids are typically used for this purpose and are introduced through an inlet in the shell into the space between the shell and the reactor tubes. Appropriate heat transfer fluids have high thermal capacity, low viscosity, are low-cost, non-toxic, and chemically inert, neither causing nor promoting corrosion of the cooling/heating system. Desirably, the heat transfer fluid will assist in the isothermal operation of the reactor, and thus, the integrity of any thermally sensitive reaction component(s) therein. Examples of suitable heat transfer fluids include, but are not limited to, molten salts such as salt carbonates, sodium (nitrite/nitrate ($NaNO_2$/$NaNO_3$) or HitecXL® (a ternary salt consisting of 48% $Ca(NO_3)_2$, 7% $NaNO_3$, and 45% $KNO_3$, oils such as Syltherm®, Dowtherm®, or water.

Figure 2:
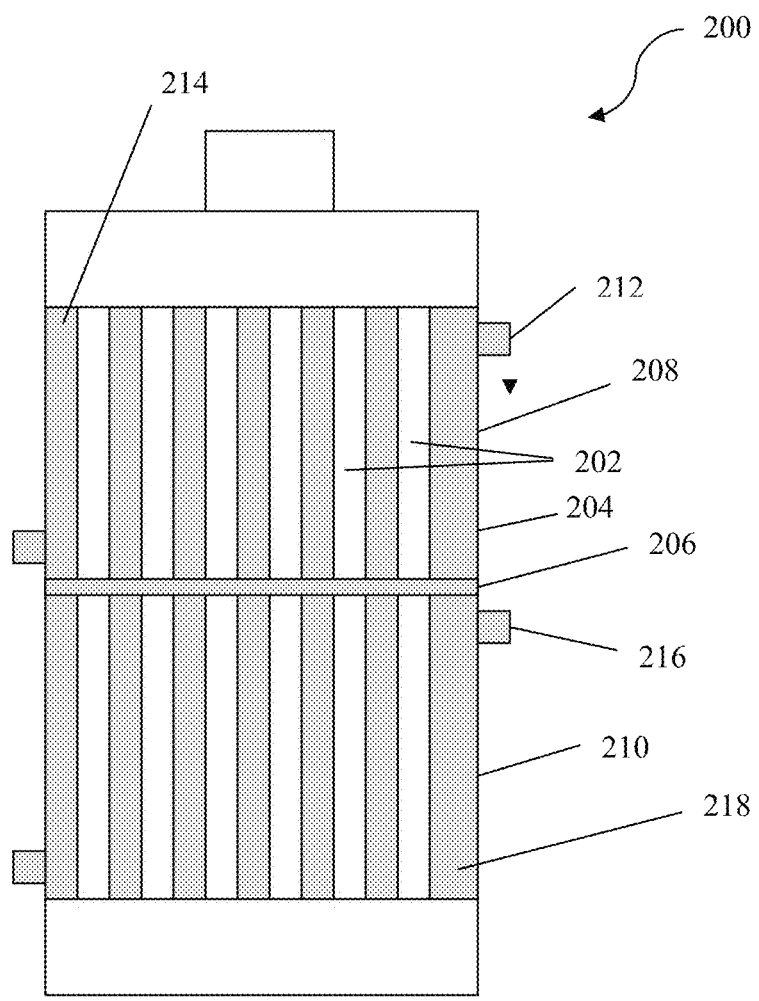
FIG. 2 is a schematic representation in cross-section of a reactor according to one embodiment of the invention.

Combinations of heat transfer fluids may be utilized. For example, in some embodiments of the present invention, the shell may be provided with one or more blind baffles, effective to thermally isolate one section of the shell/reactor tubes from another section of the shell/reactor tubes, wherein each section may be provided with the same or different heat transfer fluid. Such a reactor is shown schematically in FIG. 2. More particularly, FIG. 2 shows multitube reactor 200, comprising a plurality of reactor tubes 202 within shell 204. Baffle 206 is provided that thermally isolates reactor section 208 from reactor section 210. Heat transfer fluid inlet 212 is provided to fluidly connected space 214 with a first heat transfer fluid source (not shown). Heat transfer fluid inlet 216 is also provided, and fluidly connects space 218 to a second heat transfer fluid source (not shown).

In such embodiments, the heat transfer fluids utilized in each section may be the same or different, although the temperatures thereof may desirably differ, e.g., to facilitate the use of different temperatures within reactor sections 208 and 210. Typically, in the exemplary reaction of methyl chloride and perchloroethylene to produce 1,1,2,3-tetrachloropropene, Syltherm® or Hitec® molten salt may be used as a heat transfer fluid and may be provided through heat transfer fluid inlet 212 to space 214 at a temperature of from about 400° C.

to about 430° C., typically at a temperature of about 415° C. to assist in raising the temperature within the reactor tubes to the desired reaction temperature. Syltherm® may also be used within space 218, and may be provided thereto through heat transfer fluid inlet 216 at a temperature of from about 370° C. to about 420° C., typically at a temperature of about 395° C. The heat transfer fluid within space 218 will desirably remove heat generated by the exothermic reaction from the reaction zone, and assist maintaining the temperature therein. As such, enough reaction volume is provided to allow for sufficient residence time such that the desirable conversion percent can be achieved, while substantial byproduct formation is also minimized.

The design facilitating heat transfer within the reactor may also comprise providing a co-current flow of the desired heat transfer fluid(s) within the shell and about the reactor tubes. The use of such a co-current flow would involve providing a heat transfer fluid having a temperature appropriate to assist in preheating the feed into the reactor and reaction zone to the desired temperature, while in the reaction zone, the heat transfer fluid would desirably have a temperature sufficient to assist in the reaction zone maintaining the desired temperature. For example, for exothermic reactions as the case of the production of chlorinated and/or fluorinated propylene or higher alkene considered here, the heat transfer fluid would desirable be provided at a temperature sufficient to raise the reactor tubes and the feed to the desired temperature, and, within the reaction zone, would assist in the removal of heat therefrom, i.e., the heat transfer fluid would be at a lower temperature than the reaction zone.

Of course, the particular temperature at which the heat transfer fluid is supplied to the reactor tubes/reaction zone in this embodiment will depend upon the extent of the exothermic reaction being carried out for the production of particular chlorinated and/or fluorinated propylene or higher alkene considered here. The temperature of the heat transfer fluid may also depend upon the particular heat transfer fluid being utilized, and the desired temperature maintained. Generally speaking then, the heat transfer fluid may be caused to be at a temperature substantially equal to, or within about 50° C. higher than, the desired reaction temperature upon entry into the reactor, and within about 10° C. less than, the desired reaction temperature within a reaction zone of the reactor. That is, the heat transfer fluid may be at a temperature higher than the desired reaction upon entry into the reaction zone within the reactor and at a temperature lower than the desired reaction temperature at the end the reaction zone within the reactor since the reaction to be carried out is exothermic.

Figure 3:
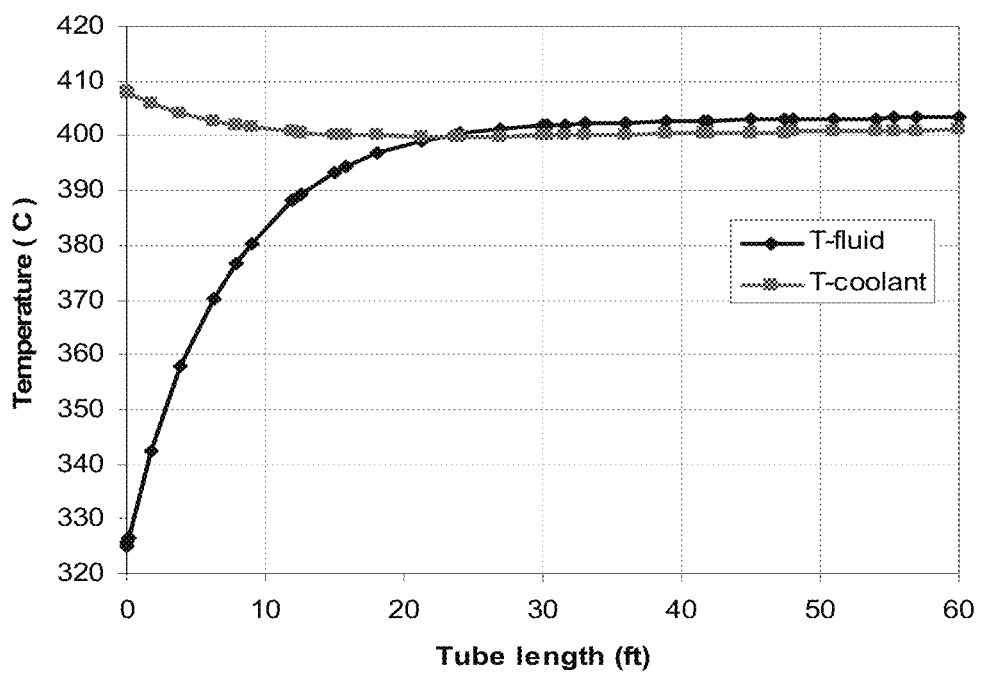
FIG. 3 is a graphical depiction of the temperature vs. tube length of a heat transfer fluid (T-coolant) in the shell and one or more reactants within the reactor tube (T-fluid) according to one embodiment of the invention.

For the exemplary exothermic reaction of methyl chloride and perchloroethylene to produce e.g., 1,1,2,3-tetrachloropropene, a molten salt, such as Dowtherm®, can be used as a heat transfer fluid, and in order to provide co-current flow, will desirably have a temperature of about 410° C. upon entry in to the reactor tubes. This temperature will desirably increase at an appropriate rate, so that by the time the heat transfer fluid reaches the reaction zone, the reaction zone is at a temperature of about 390° C. and the heat transfer fluid is at a temperature of about 405° C. This relationship is further illustrated by FIG. 3, a graph showing the relationship between the temperature of the heat transfer fluid and temperature of the reaction components and/or reactor, versus the reactor tube length for this embodiment of the invention.

In addition to the design(s) that optimize(s) heat transfer to and/or from the reactor, the reactor may also be provided with one or more designs that facilitate reduced backmixing and/or recirculation and/or reduced formation of by-products during any backmixing and/or recirculation that may occur upon exit from, the reactor.

One example of such a design involves the use of the reactor without a collector, or the redesign of any collector desirably utilized to minimize backmixing and/or recirculation zone. That is, many multitube reactors may be configured with a collector fluidly connected thereto reactor effluent is dispensed therefrom, as the case may be. Backmixing and/or recirculation may typically occur in such conventional collectors, or collectors arranged conventionally with respect to the reactor.

In order to reduce or eliminate any such backmixing and/or recirculation, the present reactors may be provided without a collector, so that the reactor effluent is passed from the reactor directly to a liquid quench zone. Or, the diameter/shape of the reactor and a collector may be configured to be substantially the same, so that areas of backmixing are not created in dead space created by disparate geometries between the reactor and collector. Any such collector will also desirably be placed about the same longitudinal axis as the reactor.

Increased residence time through conventional multitube reactors may also lead to the formation of undesirable by-products, and may generally occur due to the velocity gradient layer at the interface between an internal wall of a reactor tube and the reaction mixture flowing therethrough. The velocity of the reaction mixture in this layer is typically less than the velocity of the reaction mixture in the bulk velocity. Indeed, the velocity of the velocity gradient layer can approach zero at the reactor wall. Because of this lower velocity, reactants in this layer may experience longer residence time(s) during which unwanted side reactions may occur. Minimizing any such layer can assist in the optimization of the residence time of the reaction components within the reactor, and thus, reduced formation of by-products that may otherwise be formed.

And so, in certain embodiments of the reactors provided herein, the reactor(s) may be provided with a design that optimizes the flow of the reaction components within the velocity gradient layer. In one embodiment, this can be achieved by minimizing the depth/thickness of the layer, as can be achieved by providing a turbulence flow region within at least a portion of at least one reactor tube definable by a Reynolds number (Re) of at least about 2100. For generally circular configurations, the Reynolds number can be determined by the equation $$Re = \frac{4G}{\pi D \mu}$$

where G is the mass flow rate (kg/s), D is the tube inner diameter (m), and μ is the viscosity (1/kgr/m/s). As but one example such a configuration, a reactor with at least about 1500 tubes, wherein a majority of the tubes have an internal diameter of at least about 1.83 inches, provided with a flow rate of about 5.2e6 lbs/day therethrough, is expected to exhibit a Reynolds number of greater than about 2100 for the exemplary reaction of methyl chloride and perchloroethylene to produce 1,1,2,3-tetrachloropropene.

For embodiments of the present reactors wherein the reactor tubes are not generally circular, the Reynolds number can be determined dividing the hydraulic diameter $D_h$, which, in turn, is 4 times the cross-sectional area of flow, by the wetted perimeter, w. In such embodiments, the equation used to determine the Reynolds number would be $$Re = \frac{4G}{\pi D_h \mu},$$

wherein G is the mass flow rate (kg/s), μ is the viscosity (1/kg/m/s) and $$D_h = \frac{4A}{w}$$

where A=cross sectional area of flow and w=wetted perimeter.

In embodiments wherein such a Reynolds number is provided, the reactor design may advantageously comprise an inlet header further comprising one or more distributors that provide substantially even flow of at least one reaction component to a majority of the reactor tubes. For example, such a distributor can consist of a perforated plate having a perforation inner diameter approximately the same as the reactor tube inner diameter. Other distributor designs can include, e.g., the use of baffles, partial or full donuts, or rings arranged in the header space prior to the reactor tube inlets. If utilized, such a distributor may desirably be placed from about 2 to about 8 inches above the reactor tube inlets.

Another embodiment of a design that optimizes the flow of the reaction components at the boundary between the reaction components and at least a portion of at least one reactor tube wall may comprise minimizing the roughness of at least one reactor tube wall with one or more mechanical, electrochemical and/or chemical pretreatments. Many such treatments are known, and any of these may be utilized.

For example, mechanical pretreatments expected to minimize or reduce surface roughness of at least a portion of an internal wall of a reactor tube include, but are not limited to use of high pressure water jets, shot blasting, ceramic grinding, etc. Exemplary electrochemical pretreatments include electropolishing, e.g., HarrisonEP Electropolishing, and the like. Electropolishing involves the removal of material on an internal surface of a reactor tube by anodic dissolution. Chemical pretreatment methods include, for example, "pickling," i.e., the application of a strong acid, such as nitric and hydrofluoric acid, capable of dissolving scaling and/or other surface contaminants and the application of passivation solutions, such as citric or nitric acid.

Providing a non-reactive coating on at least a portion of an internal surface of one or more reactor tubes may also assist in a reduction in any fluid drag that may otherwise occur at the velocity gradient layer. Desirably, any such coating will be comprised of a substantially nonreactive material, or at least material less reactive than the reactor tube wall with the reaction components. Such materials are expected to include, for example, silica and carbon or graphite.

Or, an internal surface of at least a portion of one or more reactor tubes may be coated with a nanostructured coating comprising such a nonreactive material, or even a material similar in reactivity to the internal surface of the reactor tube. In this case, the nanostructure of the coating is expected to reduce the surface area and/or surface roughness of the internal surface of the reactor tube so that flow thereover by the reaction mixture is improved.

In the absence of such design provisions, or in some cases, in spite of them, by-products may be formed that can act to foul one or more reactor tube(s). As used herein, the term 'by-products' is meant to include those produced by the reaction as well as thermal decomposition products of reaction components, including in particular, any thermally sensitive components. As such, the present invention also provides embodiments in which the reactor is provided with a mechanism for applying vibration, sonic or knocking energy to the reactor, prior to, during, or after use in the process. Such mechanisms are known to those of ordinary skill in the art, as are methods for their implementation, and any of these may be used. One example of these, a sonic cleaner, is described in U.S. Pat. No. 5,912,309, hereby incorporated by reference herein for any and all purposes to the extent that it does not contradict any of the teachings herein. Desirably, whatever the mechanism employed, it will be capable of removing at least a portion of any fouling from at least a portion of at least one reactor tube wall.

The temperature of the reactor effluent is desirably reduced quickly, i.e., before any substantial amount of such by-products has had the opportunity to form. Generally speaking, and in the case of the exemplary reaction to produce 1,1,2,3-tetrachloropropene, the temperature of the reactor effluent will desirably be cooled to below 350° C. or below about 325° C. in less than about 5 seconds, or even less than about 1 second. Stated another way, the reactor effluent will desirably be cooled at a rate of at least about 15° C./s, 20° C./sec, or 50° C./sec, or even about 100° C./sec.

The desired temperature change can be effected using any suitable method of doing so at the desired rate, and in some embodiments may be accomplished via liquid quenching. In such embodiments, the quench function may be performed by any suitable method, such as, e.g., application of a temperature adjusting fluid via at least one nozzle, spray nozzle or weir nozzle.

The temperature adjusting fluid utilized in the quench function can be any suitable fluid capable of providing the desired temperature within the desired amount of time. Advantageously, the temperature adjusting fluid may be a reaction component, so that further components are not added to the process, requiring later separation and thereby adding to process cost. In some embodiments, a recycled reaction product may be utilized to perform the quench function, and may be purified, e.g., via filtration, prior to being so utilized, or may be utilized in unpurified form.

One or more of the improved design concepts may advantageously be employed in a reactor for use in a continuous gas phase, free-radical process and are expected to minimize production of by-products, including decomposition products, within the reactor. For example, any two of the design concepts may be employed, any three of the design concepts may be employed, or all four of the design concepts may be employed. Whether the reactor comprises one, two, three, or all four of the design concepts, the percent conversion of the reaction carried out within the reactor may achieve a desired range while maintaining high selectivity to the desired product, e.g., the percent conversion may at least more than 5%, with >70% selectivity to the desired product.

And so, the present multitube reactors are particularly well suited for conducting reactions for which an increase in percent conversion may typically indicate increased production of reaction by-products, and thus, reduced percent selectivity. Such reactions may also typically include at least one limiting reactant having desired conversions that are far from exhaustion, e.g., conversions of less than 80%, or less than 40%, or even less than 20%. Stated another way, at a limiting reagent conversion of at least about 5%, or at least about 10%, or at least about 15%, or even at least about 20%, selectivity to the desired product can be as high as about 70%, or about 75%, or about 80%, or even about 85% or greater. Advantageously, the reduced production of by-products can also reduce fouling of the reactor tube wall, thereby preserving reactor capacity and thus, reaction yield.

One example of a continuous, gas-phase, free radical process that may advantageously be carried out in the present reactors includes processes for the production of chlorinated and/or fluorinated alkenes comprising from about three to about six carbon atoms, in particular those making use of catalysts/initiators comprising chlorine. Such catalysts and the desired product can be thermally sensitive and can degrade or otherwise undesirably react to result in reactor fouling. Further, in the exemplary reaction of methyl chloride and perchloroethylene to produce 1,1,2,3-tetrachloropropene, the reaction product itself is not only thermally unstable, but also, prone to react further with reactants and reaction by-products to form yet other by-products.

More particularly, 1,1,2,3-tetrachloropropene is very reactive at 370° C. with methyl chloride and perchloroethylene, thermally unstable at 400° C.-500° C., and especially unstable at conventional reaction conditions for its production, i.e., at temperatures of from about 500° C. to about 750° C. The ensuing undesired reactions and/or decompositions lead to high concentrations of impurities, and ultimately thermal coking at these higher temperatures. For continuously fed, industrial reactors, coking is well known to cause further loss of reactor production capacity with time and often requires shutting down a reactor for cleaning and maintenance and thus significantly reduces productivity. Although the present invention is not so limited, reactions to produce 1,1,2,3-tetrachloropropene, as well as other similar reactions comprising reactants, products, diluents or byproducts with similar thermal sensitivity, are examples of those that can find particular benefit from application of the principles disclosed herein.

Processes performed in the present reactors can be provided with minimized production of by-products and/or decomposition products with at least 5% conversion of the limiting reagent or at least about 10%, or at least about 15%, or even at least about 20%, while maintaining selectivity to the desired product as high as about 70%, or about 75%, or about 80%, or even about 85% or greater. For example in the case of the production of 1,1,2,3-tetrachloropropene from methyl chloride and perchloroethylene, the limiting reagent perchloroethylene is expected to conversion to the desired product at 90% selectivity when converted at least 5%. And so, use of the present reactors in continuous processes for the production of chlorinated and/or fluorinated propene and higher alkenes such as 1,1,3,3-tetrachloropropene and 1,1,2-trichloro,3-fluoropropylene can provide significant time and cost savings.

The efficiencies provided by the present reactors can be further leveraged by providing the chlorinated and/or fluorinated propene and higher alkenes produced therein to further downstream processes. For example, 1,1,2,3-tetrachloropropene produced using the described reactors can be processed to provide further downstream products including hydrofluoroolefins, such as, for example, 2,3,3,3-tetrafluoroprop-1-ene (HFO-1234yf) or 1,3,3,3-tetrafluoroprop-1-ene (HFO-1234ze). Improved methods for the production of hydrofluoroolefins, 2,3,3,3-tetrafluoroprop-1-ene (HFO-1234yf) or 1,3,3,3-tetrafluoroprop-1-ene (HFO-1234ze), are thus also provided herein.

The conversion of chlorinated and/or fluorinated propene and higher alkenes to provide hydrofluoroolefins may broadly comprise a single reaction or two or more reactions involving fluorination of a compound of the formula $C(X)_m CCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of 1,1,2,3 tetrachloropropene is fluorinated in a catalyzed, gas phase reaction to form a compound such as 2-chloro-3,3,3-tri-fluoropropene. The 2-chloro-2,3,3,3-tetrafluoropropane is then dehydrochlorinated to 2,3,3,3-tetrafluoropropene via a catalyzed, gas phase reaction.

The following examples are set forth for the purpose of illustrating the invention; but these examples are not intended to limit the invention in any manner. One skilled in the art will recognize a variety of substitutions and modifications of the examples that will fall within the scope of the invention.

Example 1

Example 1A (Comparative)

A 1" ID Hastelloy reactor is heated to from about 450° C. to about 480° C. Methyl chloride and perchloroethylene flow are established at from about 50 ml/hr to about 150 ml/hr and from about 180 ml/hr to about 123 ml/hr liquid flow respectively to achieve a residence time of from about 10 seconds to about 23 seconds.

The liquid feeds are evaporated separately and preheated to achieve the same temperature as the reactor temperature in the feed line before they are mixed in ½" line before feeding into the reactor. The reactor pressure is set at about 14.7 psia. After ½" feed line, the front section (conventional mixing zone) of the 1" reactor was filled with Rashig rings at a depth of 2 inches to provide at least approximated plug flow and proper mixing.

Within about three hours, a hot spot of about 600° C. was measured and graphite was formed in the mixing zone, plugging the reactor. It appears that the temperature and the backmixing and/or recirculation flow profile created in the conventional mixing area (where the ½" mixer goes into the 1" flow straightener zone filled with Rashig rings) induced unwanted reactions to produce the by-products that were deposited this zone.

This example thus shows that the existence of backmixing and/or recirculation in the reactor at the intended reaction temperature results in low selectivity to desired product and close to zero reactor productivity that renders the process uneconomical.

Example 1B

Another run in accordance with Example 1A produced at least 8% conversion of perchloroethylene at more than 90% selectivity to 1,1,2,3-tetrachloropropylene after the mixing temperature is reduced to 325° C., the 2 inch mixing zone is removed, and the heating zone is moved down stream at least 6-inches away from the entrance of the feed line of the reactor. This run shows that 325° C. is sufficiently low for the reaction kinetics to avoid the production of byproducts and carbon deposits in the zone just after the feed entrance to the reactor.

Example 2

Chlorinated and/or fluorinated propenes having the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while c+g<2, d+h<1, and e+f<3 are prepared using a reactor utilizing an inlet temperature deviating from the desired reaction temperature by at least about 20° C. as follows. About 3000 schedule 40 1.5" ID tubings at 60 ft long are used in this example. The desired feed, which will depend upon the desired chlorinated and/or fluorinated propene being prepared is provided to an isothermal multitube reactor. The feed is provided at a temperature that differs from the desired reaction temperature by at least about 20° C. by controlling the temperature of the inlet and/or controlling the temperature of the feeds. It is expected that the selectivity will decrease as the feed temperature is raised closer to the reaction temperature of around 375° C.

TABLE 1

| Example | Feeds | Feed Temp (° C.) | Hx Inlet temp (° C.) | Hx fluid type | Selectivity | Productivity (kTA) |
|---|---|---|---|---|---|---|
| Comparative | Methyl chloride perchloroethylene | 325 | 410 | Dow therm | 89.2% | 43.7 |
| 1A | Methyl chloride perchloroethylene | 350 | 400 | Dowtherm | 89.4% | 42.7 |
| 1B | Methyl chloride perchloroethylene | 275 | 430 | Hitec MS | 89.7% | 41.6 |

Example 3

Chlorinated and/or fluorinated propenes having the formula $CH_{2-c-g}Cl_cF_g$=$H_{1-d-h}Cl_dF_h$—$CH_{3-e-f}Cl_eF_f$ wherein c is 0-2, d is 0-1, e is 0-3, f is 0-3, and g is 0-2 while c+g<2, d+h<1, and e+f<3, are prepared using a reactor utilizing an inlet temperature deviating from the desired reaction temperature by at least about 20° C. as follows. The desired feeds, which will depend upon the desired chlorinated and/or fluorinated propene being prepared, is provided to an isothermal multi-tube reactor. The feed is provided at a temperature that differs from the desired reaction temperature by at least about 20° C. by controlling the temperature of the inlet and/or controlling the temperature of the feeds.

TABLE 2

| Example | Feeds | Feed Temp (° C.) | Inlet temp (° C.) | Reaction Temp (RT, ° C.) | % Conversion | % Selectivity |
|---|---|---|---|---|---|---|
| Comparative | $CH_{4-a-b}Cl_aF_b$ $CH_{4-a-b}Cl_aF_b$ | RT | RT | RT | ≤10% | X % |
| 1A | $CH_{4-a-b}Cl_aF_b$ $CH_{4-a-b}Cl_aF_b$ | RT − 20° C. | RT-20° C. | RT | ≤15% | >X % |
| 1B | $CH_{4-a-b}Cl_aF_b$ $CH_{4-a-b}Cl_aF_b$ | RT − 50° C. | RT-50° C. | RT | ≤15% | >X % |

Example 4

The chlorinated and/or fluorinated propenes shown in Table 3, below, are prepared using a reactor as shown in FIG. 2. More particularly, chlorinated and/or fluorinated propenes having the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g<2, d+h<1, and e+f<3, are prepared by providing feeds having the formula $CH_{4-a-b}Cl_aF_b$ to an isothermal multitube reactor. A heat transfer fluid is used in a first reactor zone (space 214, FIG. 2) to maintain a first desired temperature and the same, or a different, heat transfer fluid is used in a second reactor zone to maintain a second desired temperature. The flow of the heat transfer fluids may be co-current (CoC), or countercurrent (CC). As shown, the % conversion (% Conv) will not substantially increase. For the comparative example, the reactor only comprises one zone. In Table 3, and the remaining tables, "Conv" means conversion and "Sel" means selectivity.

TABLE 3

| Example | Heat transfer fluid, first zone | First Reactor zone temp (° C.) | Heat transfer fluid, second zone | Second Reactor zone temp (° C.) | Flow | % Conv. | % Sel. |
|---|---|---|---|---|---|---|---|
| Comp | Molten salt | 410 | NA | NA | NA | 10.7 | X % |
| 2A | Molten salt | 400° C.-430° C. | Molten salt | 370° C.-400° C. | CoC | ≤15% | >X % |
| 2B | Water | 400° C.-430° C. | Water | 370° C.-400° C. | CC | ≤15% | >X % |
| 2C | Molten salt | 400° C.-430° C. | Water | 370° C.-400° C. | CoC | ≤15% | >X % |
| 2D | Syltherm ® | 415° C. | Hitec ® | 395° C. | CC | ≤15% | >X % |
| 2E | Syltherm ® | 415° C. | Syltherm ® | 395° C. | CoC | ≤15% | >X % |
| 2F | Hitec ® | 415° C. | Syltherm ® | 395° C. | CC | ≤15% | >X % |

Example 5

Methyl chloride, perchloroethylene and carbon tetrachloride were fed to a 2" ID Inconel 600 reactor at the rate of 3500-4500 SCCM, 1400-17000 SCCM, and 700-980 SCCM respectively to achieve about 30-40 seconds residence time at 260 psig. The reactor effluent at 410-420° C. is cooled down at 270-350° C. at a residence time of about less than 10 seconds before condensed in a 0.5 inch ID cooling coil at temperature of less than 80° C. After a week of run time at low Perc conversion of 3.8-5.0%, the reactor is shutdown due to plugging in the outlet reactor due to severe fouling at the cool down zone and the condensing coil. Replacing the cool down zone and condensing coil with a liquid spray quench chamber resulted in run time of more than two weeks at twice the limiting reagent conversion. Opening the reactor shows no fouling in the spray quench chamber.

This example thus shows that rapid quenching of greater than 15° C./s is required to minimize fouling in the product quenching zone.

Example 6

Chlorinated and/or fluorinated propenes are prepared using a reactor which has been modified to reduce any backmixing that may otherwise occur in a collector operatively disposed relative thereto, and/or to minimize the impact of any backmixing that may occur. More particularly, chlorinated and/or fluorinated propenes having the formula $CH_{2-c-g}Cl_cF_g=CH_{1-d-h}Cl_dF_h—CH_{3-e-f}Cl_eF_f$ wherein c is 0-2, d is 0-1, e is 0-3, f is 0-3, and g is 0-2 while c+g<2, d+h<1, and e+f<3, are prepared by providing feeds having the formula $CH_{4-a-b}Cl_aF_b$ to an isothermal multitube reactor. The collector is modified to have the same diameter/shape as the reactor, and in some embodiments, the quench shown in Table 4 is provided.

TABLE 4

| Example | Feeds | Collector | Quench | % Conversion | % Selectivity |
|---|---|---|---|---|---|
| Comp | $CH_{4-a-b}Cl_aF_b$ $CH_{4-a-b}Cl_aF_b$ | Conventional | No | X % | X % |
| 3A | $CH_{4-a-b}Cl_aF_b$ $CH_{4-a-b}Cl_aF_b$ | Modified | No | X % + ≤5% | >X % |
| 3B | $CH_{4-a-b}Cl_aF_b$ $CH_{4-a-b}Cl_aF_b$ | None | Yes, Weir | X % + ≤5% | >X % |
| 3C | $CH_{4-a-b}Cl_aF_b$ $CH_{4-a-b}Cl_aF_b$ | Modified | Yes | X % + ≤5% | >X % |
| 3D | Methyl chloride Perchloroethylene | Modified | No | X % + ≤5% | >X % |
| 3E | Methyl chloride Perchloroethylene | None | Yes, Weir | X % + ≤5% | >X % |
| 3F | Methyl chloride Perchloroethylene | Modified | Yes | X % + ≤5% | >X % |

Example 7

Chlorinated and/or fluorinated propenes are prepared using a reactor which has been modified to optimize the flow of the reaction components within the velocity gradient layer, as shown in Table 5. More particularly, chlorinated and/or fluorinated propenes having the formula $CH_{2-c-g}Cl_cF_g=CH_{1-d-h}Cl_dF_h—CH_{3-e-f}Cl_eF_f$ wherein c is 0-2, d is 0-1, e is 0-3, f is 0-3, and g is 0-2 while c+g<2, d+h<1, and e+f<3, are prepared by providing feeds having the formula $CH_{4-a-b}Cl_aF_b$ to an isothermal multitube reactor. Modification of the feed distributor to improve mixing and distribution of the feed to all the tubes in the reactors is expected to improve selectivity at the same level of limiting reagent conversion. Similarly, better selectivity is also expected when reactor tube wall is pretreated or coated to reduce surface roughness and thus decrease the boundary layer thickness where the low velocity/laminar zone where the byproducts and fouling are expected to occur.

TABLE 5

| Example | Feed Distributor | Pretreatment | Coating | Selectivity |
|---|---|---|---|---|
| Comp | No | No | No | 89.7% |
| 4A | Yes, perforated plate | No | No | >89% |
| 4B | Yes, baffles | No | No | >89% |
| 4C | Yes, donuts | No | No | >89% |
| 4D | No | Yes, mechanical | No | >89% |
| 4E | No | Yes, electrochemical | No | >89% |
| 4F | No | Yes, chemical | No | >89% |
| 4G | No | No | Yes, carbon | >89% |
| 4H | No | No | Yes, graphite | >89% |
| 4I | No | No | Yes, nanostructured | >89% |
| 4J | Yes | Yes | No | >89% |
| 4K | No | Yes | Yes | >89% |
| 4L | Yes | No | Yes | >89% |
| 4M | Yes | Yes | Yes | >89% |

Example 8

Hydrofluoroolefins are prepared from the chlorinated and/or fluorinated propenes prepared according to Examples 1-4 by any of several methods known in the art. For example, the conversion of 1,1,2,3-tetrachlororopropene to HFO-1234yf using HF with Chromium/Cobalt base catalyst may be prepared in accordance with the methodology described in WO2008054781A1. WO 2009003084 describes a multi-step process wherein a feedstock of 1,1,2,3 tetrachloropropene is fluorinated in a liquid phase without a catalyst followed by a catalyzed, gas phase reaction to form 2-3,3,3-tetrafluoropropene (HFO1234yf) that is also suitable. US20090030244A1 describes the production of HFO-1234yf using 1,1,2,3-tetrachloropropene using a catalytic process with HF with HCFC-1233xf as intermediate, and this process may also be used. Finally, US20090099396A1 describes a suitable a liquid phase catalytic reaction followed by gas-phase reaction of 1,1,2,3-tetrachloropropene with HV with HFC-245eb as an intermediate. Each of these patent documents is hereby incorporated by reference herein in its entirety for any and all purposes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An isothermal multitube reactor comprising a plurality of reactor tubes situated within a shell and suitable for use in a continuous, gas phase, free radical process for the production of chlorinated and/or fluorinated propene and higher alkenes from the reaction of chlorinated and/or fluorinated alkanes and chlorinated and/or fluorinated alkenes, wherein the reactor comprises a collector configured to accept reactor effluent from the reactor and further configured to minimize backmixing, comprises a temperature reduction mechanism operatively disposed relative to the inlet or feed(s) and wherein at least a portion of at least one reactor tube is definable by a Reynolds number of at least about 2100.

2. The reactor of claim 1, wherein the reactor comprises a design that minimizes the production of by-products, wherein the reactor design comprises one or more of: i) a design that facilitates heat transfer to and/or from the reactor; ii) a design that facilitates reduced backmixing upon exit from, the reactor, and/or reduced formation of by-products during any backmixing that may occur; iii) a design that optimizes the flow of the reaction components at a boundary between the reaction components and at least a portion of at least one reactor tube wall; and/or iv) a design that facilitates a reduction of the temperature of a reactor effluent to a temperature below which substantial formation of by-products does not occur.

3. The reactor of claim 2, wherein the reactor design comprises i) a design that facilitates heat transfer to and/or from the reactor; ii) a design that facilitates reduced backmixing upon exit from, the reactor, and/or reduced formation of by-products during any backmixing that may occur; iii) a design that optimizes the flow of the reaction mixture at a boundary between the reaction mixture and at least a portion of at least one reactor tube wall; and iv) a design that facilitates a reduction in temperature of a reactor effluent to a temperature at which substantial formation of by-products does not occur.

4. The reactor of claim 2, wherein the design facilitating heat transfer comprises the shell being partitioned into at least two sections, so that different temperatures can be maintained within each section.

5. The reactor of claim 2, wherein the design comprises an inlet header further comprising one or more distributors that provide a substantially even flow of at least one reaction component to a majority of the reactor tubes.

6. The reactor of claim 2, wherein at least one reactor tube wall is subjected to a pretreatment to minimize surface roughness prior to utilization of the reactor in the desired reaction, with one or more mechanical, electrochemical and/or chemical pretreatments.

7. The reactor of claim 2, wherein at least a portion of at least one reactor tube wall is coated with a coating that minimizes the deposition of foulants.

8. The reactor of claim 2, wherein the reactor is operably disposed relative to a source of vibration, sonic or knocking energy.

9. The reactor of claim 2, wherein the design that facilitates a reduction of the temperature of a reactor effluent comprises a liquid quench function.

10. The reactor of claim 1, wherein at least a portion of at least one reactor tube wall is coated with a coating that minimizes the deposition of foulants so that the reactor is suitable for use in a continuous, gas phase, free radical process comprising at least one thermally sensitive component.

* * * * *